United States Patent
Hurst

(10) Patent No.: US 6,671,628 B2
(45) Date of Patent: Dec. 30, 2003

(54) METHODS FOR IDENTIFYING A MOLECULE THAT MAY BIND TO A TARGET MOLECULE

(75) Inventor: John R. Hurst, San Diego, CA (US)

(73) Assignee: ChemNavigator, Inc., San Diego, CA (US)

(*) Notice: Subject to any disclaimer, the term of this patent is extended or adjusted under 35 U.S.C. 154(b) by 0 days.

(21) Appl. No.: 10/213,122

(22) Filed: Aug. 5, 2002

(65) Prior Publication Data

US 2003/0167136 A1 Sep. 4, 2003

Related U.S. Application Data

(63) Continuation-in-part of application No. 10/192,763, filed on Jul. 8, 2002.
(60) Provisional application No. 60/362,629, filed on Mar. 4, 2002.

(51) Int. Cl.$^7$ .......................... G01N 31/00; G06F 19/00
(52) U.S. Cl. ........................................... 702/27; 703/11
(58) Field of Search ..................... 702/19–25, 27–32; 703/2, 11, 12

(56) References Cited

U.S. PATENT DOCUMENTS

| | | | |
|---|---|---|---|
| 5,307,287 A | 4/1994 | Cramer, III et al. | 703/2 |
| 5,386,507 A | 1/1995 | Teig et al. | 345/836 |
| 5,751,605 A | 5/1998 | Hurst et al. | 702/27 |
| 5,752,019 A | 5/1998 | Rigoutsos et al. | 707/3 |
| 5,787,279 A | 7/1998 | Rigoutsos | 707/6 |
| 5,866,343 A | 2/1999 | Blom et al. | 435/7.1 |
| 6,226,603 B1 * | 5/2001 | Freire et al. | 703/11 |
| 6,230,102 B1 | 5/2001 | Tidor et al. | 702/19 |
| 6,308,145 B1 | 10/2001 | Itai et al. | 703/12 |
| 2001/0000807 A1 | 5/2001 | Freire et al. | 703/12 |
| 2001/0018682 A1 | 8/2001 | Itai et al. | 707/1 |
| 2001/0034580 A1 | 10/2001 | Skolnick et al. | 702/19 |
| 2001/0056329 A1 | 12/2001 | Smellie et al. | 702/27 |
| 2002/0099506 A1 * | 7/2002 | Floriano et al. | 702/19 |

OTHER PUBLICATIONS

Hurst, T. Flexible 3D Searching: The Directed Tweak Techniqe, 1994, J. Chem. INf. Comput. Sci. 34: 190–196.*
Badel, A. et al. (1992). "Searching for Geometric Molecular Shape Complementarity Using Bidimensional Surface Profiles," *J. Mol. Graphics* 10:205–211.
Badel–Chagnon, A. et al. (1994). "'Iso–Depth Contour Map' of a Molecular Surface," *J. Mol. Graphics* 12:162–168.
Bohm, H–J. (1994). "The Development of a Simple Empirical Scoring Function to Estimate the Binding Constant For a Protein–Ligand Complex of Known Three–Dimensional Structure," *Journal of Computer–Aided Molecular Design* 8:243–256.
Connolly, M. "Molecular Surfaces: A Review," located at <http://www.netsci.org/Science/Compchem/feature14.html> visited on Oct. 22, 2002, two pages.

Dixon, J.S. (1997). "Evaluation of the CASP2 Docking Section," *Proteins: Structure, Function and Genetics* Supplement 1: 198–204.
Edelsbrunner, H. and Mücke, E.P. (1994). "Three–Dimensional Alpha Shapes," *ACM Transactions on Graphics* 13(1): 43–72.
Gasteiger, J. and Marsili, M. (1978). "A New Model for Calculating Atomic Charges in Molecules," *Tetrahedron Letters* 34: 3181–3184.
Gehlhaar, D.K. et al. (1995). "Molecular Recognition of the Inhibitor AG–1343 by HIV–1 Protease: Conformationally Flexible Docking by Evolutionary Programming," *Chemistry & Biology* 2(5):317–324.
Hurst, T. (1994). "Flexible 3D Searching: The Directed Tweak Technique," *J. Chem Inf. Comput. Sci.* 34: 190–196.
Hurst, T. (2002). "Evaluating Protein–Ligand Interactions Through Flexible Docking," Abstract, only one page.
Jackson, R.M. et al. (1998). "Rapid Refinement of Protein Interfaces Incorporating Solvation: Application to the Docking Problem," *Journal of Molecular Biology* 276: 265–285.
Jones, G. et al. (1995). "Molecular Recognition of Receptor Sites Using a Genetic Algorithm with a Description of Desolvation," *Journal of Molecular Biology* 245: 43–53.
Jones, G. et al. (1997). "Development and Validation of a Genetic Algorithm for Flexible Docking," *Journal of Molecular Biology* 267: 727–748.
Ladbury, J.E. (1996). "Just Add Water! The Effect of Water on the Specificity of Protein–Ligand Binding Sites and its Potential Application to Drug Design," *Chemistry & Biology* 3(12): 973–980.
Lam, P. Y.S. et al. (1994). "Rational Design of Potent, Bioavailable, Nonpeptide Cyclic Ureas as HIV Protease Inhibitors," *Science* 263: 380–384.
Leach, A.R. (1994). "Ligand Docking to Proteins With Discrete Side–Chain Flexibility," *Journal of Molecular Biology* 235: 345–356.
Merritt, E.A. et al. (1994). "Crystal Structure of Cholera Toxin B–Pentamer Bound to Receptor $G_{M1}$ Pentasaccharide," *Protein Science* 3: 166–175.
Morris, G.M. et al. (1998). "Automated Docking Using a Lamarckian Genetic Algorithm and an Empirical Binding Free Energy Function," *Journal of Computational Chemistry* 19(14): 1639–1662.
Oshiro, C.M. et al. (1995). "Flexible Ligand Docking Using a Genetic Algorithm," *Journal of Computer–Aided Molecular Design* 9: 113–130.

(List continued on next page.)

Primary Examiner—Marc S. Hoff
Assistant Examiner—Manuel L Barbee
(74) Attorney, Agent, or Firm—Morrison & Foerster LLP

(57) ABSTRACT

Methods which may be implemented in computer systems for screening a database of candidate molecules to determine whether any particular subset of candidate molecules may be docked to a target molecule. These methods determine the force field of a target molecule only once and may be used for screening a large number of candidate molecules.

10 Claims, No Drawings

OTHER PUBLICATIONS

Rarey, M. et al. (1999). "The Particle Concept: Placing Discrete Water Molecules During Protein–Ligand Docking Predictions," *Proteins: Structure, Function, and Genetics* 34: 17–28.

Raymer, M.L. et al. (1997). "Predicting Conserved Water–Mediated and Polar Ligand Interactions in Proteins Using a K–Nearest–Neighbors Genetic Algorithm," *Journal of Molecular Biology* 265: 445–464.

Schnecke, V. et al. (1998). "Screening a Peptidyl Database for Potential Ligands to Proteins With Side–Chain Flexibility," *Proteins: Structure, Function, and Genetics* 33: 74–87.

Schnecke, V. and Kuhn, L.A. (1999). "Database Screening for HIV Protease Ligands: The Influence of Binding–Site Conformation and Representation on Ligand Selectivity," *Proceedings of the Seventh International Conference on Intelligent Systems for Molecular Biology* Lengauer, T. et al eds. AAAI Press, Menlo Park, CA pp 242–251.

Schnecke, V. and Kuhn, L.A. (1999). "Flexibly Screening For Molecules Interacting with Proteins," *Rigidity in Theory and Applications* Thorpe, M.F. and Duxbury, P.M. eds. Plenum Publishing, New York, NY pp. 385–400.

Shanno, D.F. (1978). "Conjugate Gradient Methods with Inexact Searches," *Mathematics of Operations Research* 3(3): 244–256.

Shoichet, B.K. et al. (1992). "Molecular Docking Using Shape Descriptors," *Journal of Computational Chemistry*, 13(3): 380–397.

Shoichet, B.K. et al. (1999). "Ligand Solvation in Molecular Docking," *Proteins: Structure, Function, and Genetics* 34: 4–16.

Venkatachaiam, C.M. et al. (1991). "Flexible Fitting of Target Molecules to 3D Pharmacophore Models," *Infornortics* Presented at the Montreux 1991 International Chemical Information Conference, Annecy, Switzerland. Four pages.

Wasserman, Z.R. and Hodge, C.N. (1996). "Fitting An Inhibitor Into The Active Site of Thermolysin: A Molecular Dynamics Case Study," *Proteins: Structure, Function, and Genetics* 24: 227–237.

Welch, W. et al. (1996). "Hammerhead: Fast, Fully Automated Docking of Flexible Ligands to Protein Binding Sites," *Chemistry & Biology* 3(6): 449–462.

* cited by examiner

METHODS FOR IDENTIFYING A MOLECULE THAT MAY BIND TO A TARGET MOLECULE

CROSS-REFERENCE TO RELATED APPLICATIONS

This application is a continuation in part of the U.S. utility application Ser. No 10/192,763 filed on Jul. 8, 2002, with inventor Tad Hurst, title METHOD OF SCREENING A DATABASE OF SMALL MOLECULES TO DETERMINE POTENTIAL BINDING TO A LARGE MOLECULE, which application is incorporated herein by reference. This application claims the benefit of U.S. Provisional Application Serial No. 60/362,629, filed on Mar. 4, 2002, with inventor Tad Hurst and title, METHOD OF SCREENING A DATABASE OF SMALL MOLECULES TO DETERMINE POTENTIAL BINDING TO A LARGE MOLECULE, which application is incorporated herein by reference.

FIELD OF THE INVENTION

Methods and systems described in this patent generally relate to methods and systems for identifying candidate molecules that may bind to a target molecule. Methods described in this patent may be implemented in a computer system and may be embodied as computer programs in an article of manufacture. The methods and systems described in this patent also relate to methods and systems for determining from a set of candidate molecules those molecules that may bind to a target molecule.

BACKGROUND OF THE INVENTION

Drug discovery may be conceptually understood in two steps: 1) target identification and 2) lead identification and optimization. In the first step of target identification, a large molecule, which may be but is not limited to a cell-surface receptor or intra-cellular protein, referred to as the target, may be identified with a particular biological pathway or structure of interest. Once a potential target has been identified, it must be screened against a large number of small molecules to determine whether the target is drugable—i.e. whether any small molecules can be found to bind or interact with the target. Lead identification is very expensive and time consuming, often involving experimentally screening a target against many millions of small molecules to determine binding affinities. Once one or more drug leads to a target have been identified, it is still often necessary to optimize a lead in order to improve its pharmacological efficacy. In this step, referred to as lead optimization, synthetic chemists chemically modify the lead in order to increase or decrease its binding to the target, modify its susceptibility to degradative pathways, or modify its pharmacokinetics.

The current combinatorial methods of lead identification and to a lesser extent, lead optimization, could be improved if rationalized. Rational lead optimization, as used herein, refers to using theoretical methods to determine a set of likely lead candidates to a given target before experimentally screening lead-target binding. Rational lead optimization offers the possibility of reducing drug discovery time and expenses by reducing the number of potential lead-target screens.

Early methods of rational lead optimization sought to find a set of potential leads from a database of small molecules chemically similar to a known lead. The earliest of these techniques was performed by the synthetic chemist in the process of producing the next substance to test. The chemist would make a set of small changes to the structure and determine if those changes had a beneficial or detrimental effect on the efficacy. This process, called analog synthesis, is effective, although time-consuming and expensive. Analog synthesis is the basis for medicinal chemistry, and remains an important part of drug discovery today.

Early attempts at using computers to make the lead optimization process more efficient involved determining chemical similarity between a potential lead and a known lead using graph-theoretical treatments. Methods of this type include searching a database of compounds for those that contain the same core structure as the lead compound—called substructure searching or two-dimensional (2-D) searching—and searching for compounds that are generally similar based on the presence of a large number of common fragments between the potential lead expansion compound and the lead compound—called 2-D similarity searching. These techniques are somewhat effective, but are limited to finding compounds that are obviously similar to the lead, thus affording the medicinal chemist few new insights for directing the synthesis project.

Another technique using computers makes use of the knowledge of how the small molecules bind to the large molecule. There are often special groups called pharmacophore groups that are responsible for most of the stabilization energy of the complex. The three-dimensional (3-D) searching techniques try to find from a large database of potential lead compounds those that have essentially the same geometrical arrangement of pharmacophore groups as the lead compound. The 3-D arrangement of the pharmacophore groups required for interaction with the large molecule is called a pharmacophore model or 3-D query. Compounds that are found to contain the correct arrangement are called "hits," and are candidates for screening. These hits differ from the substructure or 2-D similarity hits in that the backbone of the structure may be quite different from that of the original lead compound, and often represents an important new area of chemistry to be explored.

The simplest of the 3-D searching techniques compares the position and arrangement of the pharmacophore groups of 3-D structures as stored in the database. This is referred to as static 3-D searching. A fairly obvious shortcoming to determining chemical similarity from a database of small molecules of fixed geometry is that molecules often do not have rigid structures, but rather have a large number of accessible conformations formed from rotating the molecular framework of a molecule about its single bonds. These bonds that can easily be rotated are referred to as rotatable bonds. As used herein, molecular configurations defined by rotations about the dihedral angles of its rotatable bonds will be referred to as rotamers. Small molecules in pharmaceutical database typically contain an average of six to eight rotatable bonds per molecule. This can easily afford a set of accessible rotamers that number in the millions. Searching just one static conformation (rotamer) from among millions of possible rotamers for the correct arrangement of groups will cause many compounds that could be good leads to be missed.

In order to consider energetically accessible rotamers, early small molecule databases often contained a small subset of the accessible rotamers of each small molecule. Herein, this technique is called multi-conformational 3-D searching. However, attempting to define individually each rotamer for a given small molecule quickly becomes impractical as the number of atoms in a given small molecule increases. Accordingly, other early methods of searching small molecule databases for potential target leads attempted to define a conformation space for each small molecule. See U.S. Pat. No. 5,752,019.

A further extension of 3-D search technology involves investigation of the accessible conformational space of the potential hits as part of the searching process. These techniques, called conformationally flexible 3-D searching techniques, adjust the conformation of the potential hit according to the requirements of the 3-D pharmacophore query. One such technique that has been found to be effective uses a method called "Directed Tweak". See Hurst, T. *Flexible 3D Searching: The Directed Tweak Technique*, 34, J. Chem. Inf. Comput. Sci. 190 (1994). This method is very effective for finding molecules of interest when the geometry of the binding site of the large molecule is not known. Directed Tweak adjusts the conformation of the small molecule by changing the angle values of the rotatable bonds. This method therefore ignores changes in conformation because of bond stretching and bond bending. Bond stretching vibrations for molecules near room temperature typically change the length of a bond by about 0.05 Angstroms (Å). Bond bending between three connected atoms typically moves one of the atoms by about 0.1 Å. Rotation about rotatable bonds often moves atoms by several Ås or tens of Ås. Thus, adjusting only the rotatable bond values includes essentially all of the accessible conformational flexibility of a small molecule.

When the binding site of the target protein is known, another way to identity potential leads is by docking potential leads into the binding site. Docking approaches can be classified based on how they characterize the ligand-binding site of the protein. Grid-search techniques fill the space around the binding site with a 3-D grid, precompute the potentials (van de Waals, electrostatic, etc.) at each grid point without a ligand, then sample different ligand conformations and orientations on the grid and compute the resulting binding energy.

Early attempts of rational lead optimization modeled small molecule docking to a target using molecular mechanics force field methodologies. Molecular mechanics methodologies (also called force field methodologies) attempt to model the short range and long range forces between a target and a small molecule using field representations. U.S. Pat. No. 5,866,343, treats the target and small molecule using separate potential energy fields. Each potential energy field comprises a 1/R long range electrostatic contribution and a short range 6–12 Lennard-Jones contribution. The interaction energy between a target and a small molecule is then calculated for the position of the small molecule relative to the large one. The position is then adjusted iteratively so as to give lower and lower energies. This continues until a low energy arrangement is found. Another example is AutoDock (Morris, G. M., Goodsell, D. S., Halliday, R. S., Huey, R., Hart, W. E., Belew, R. K. and Olson, A. J. "Automated Docking Using a Lamarckian Genetic Algorithm and Empirical Binding Free Energy Function", *J. Computational Chemistry*, 19(1998), 1639–1662.) which uses simulated annealing in its previous releases, but now applies a hybrid genetic algorithm to sample over the feasible binding nodes of the ligand relative to the protein. The advantages of grid-based docking are that a template of favorable interactions in the ligand-binding site does not need to be defined, thus reducing bias in modeling the protein-ligand interactions, and evaluation of binding modes is made more efficient by precomputing the potential energy that results from interaction with the protein at each point on the grid. However, the accuracy and timing of this approach depends on the grid fineness, making this approach too computationally intensive for database screening, in which thousands of molecules (as well as ligand orientations and shapes, or conformers) need to be tested. Furthermore, precomputation of the protein grid potentials limits this approach to rigid binding sites.

When a ligand-binding site in a protein is known, a grid template may be used by constructing a template for ligand binding based upon favorable interaction points in the binding site. During the search for a favorable ligand-binding mode, different conformations of the ligand can be generated and subsets of its atoms matched to complementary template points as a basis for docking the ligand into the binding site. One of the principal advantages to a template-based approach is that a template can incorporate known features of ligand binding (for example, conserved interactions observed experimentally for known ligands). Thus, the docking search space is reduced to matching N ligand atoms onto N template points, rather than the six-dimensional orientational search space (three degrees of rotational freedom and three degrees of translational freedom) required in other approaches for sampling and evaluating ligand binding.

Another well-known docking tool is DOCK (Schoichet, B. K., Bodian, D. L., and Kuntz, I. D., *J. Comput. Chem.* 13 (1992) 380). In this program the template typically consists of up to 100 spheres that generate a negative image of the binding site. During the search, subsets of ligand atoms are matched to spheres, based on the distances between ligand atoms. DOCK has been extended to consider chemistry and include hydrogen-bonding interaction centers in addition to the shape template. Other current template approaches specify a set of interaction points defining favorable positions for placing polar ligand atoms or hydrophobic (nonpolar) centers, e.g., aromatic rings. Such a template can be generated automatically, e.g., by placing probe points on the solvent accessible surface of the binding site, or interactively by superimposing known protein-ligand complexes to identify favorable interaction points based on observed binding modes for known ligands. Another docking program, FlexX (licensed by Tripos Inc.—1699 South Hanley Road, St. Louis, Mo. 63144-2913, phone: 314-647-1099) uses a template of 400 to 800 points when docking small molecules (up to 40 atoms, not including hydrogens) to define positions for favorable interactions of hydrogen-bond donors and acceptors, metal ions, aromatic rings, and methyl groups. The ligand is fragmented and incrementally reconstructed in the binding site and matched to template points based on geometric hashing (indexing) techniques, bond torsional flexibility is modeled discretely, and a tree-search algorithm is used to keep the most promising partially constructed ligand conformations during the search. Hammerhead (Welch W, Ruppert J, Jain AN. 1996. Hammerhead: Fast, fully automated docking of flexible ligands into protein binding sites. *Chem Biol* 3(1996), 449–462.) uses up to 300 hydrogen-bond donor and acceptor and steric (van der Waals interaction) points to define the template, and the ligand is incrementally constructed, as in FlexX. A fragment is docked based on matching ligand atoms and template points with compatible internal distances, similar to the matching algorithm used in DOCK. If a new fragment is positioned closely enough to the partially constructed ligand, the two parts are merged, and the most promising placements kept.

Other successful docking approaches, such as GOLD (G. Jones, P. Willett, R. C. Glen, A. R. Leach & R. Taylor, J. Mol. Biol 267 (1997) 727–74.), and the method of Oshiro et al. (Oshiro C, Kuntz I, Dixon J. *Flexible ligand docking using a genetic algorithm*. J Comput Aided Mol Des 1995;9:113–130.) use genetic algorithms to sample over possible matches of conformationally flexible ligands to the template. GOLD uses a template based on hydrogen-bond donors and acceptors of the protein and applies a genetic algorithm to sample over all possible combinations of intermolecular hydrogen bonds and ligand conformations. However, a drawback of genetic algorithm approaches, including AutoDock, is the high computation time, especially in comparison to fragment-based docking approaches.

The UNITY 3-D searching system (licensed by Tripos Inc.—1699 South Hanley Road, St. Louis, Mo. 63144-2913, phone: 314-647-1099) has been extended to provide what is essentially a docking tool. In this approach, six parameters corresponding to the six rotational/translational degrees of freedom are added to the rotatable bond list, and these parameters are adjusted to place pharmacophoric groups at the positions giving favorable interactions with the receptor. This method produces acceptable accuracy, but is time consuming because the derivatives needed for the minimization must be calculated numerically. Each derivative calculation requires three or more small adjustments to the geometry of the small molecule.

Another current docking method, SPECITOPE (Volker Schnecke, Craig A. Swanson, Elizabeth D. Getzoff, John A. Tainer, and Leslie A. Kuhn, Screening a Peptidyl Database for Potential Ligands to Proteins with Side-chain Flexibility Proteins: Structure, Function, and Genetics, Vol. 33, No. 1, 1998, 74–87) combines grid methods with adaptive geometry techniques in order to model protein side chain flexibility. SPECITOPE uses a binding site template to limit the orientational search for each prospective ligand and uses distance geometry techniques to avoid the computationally intensive fitting of infeasible ligands into a binding site. The speed gained by distance geometry methods allows the modeling of protein side chain flexibility during docking.

The results of fast docking tools to predict ligand binding modes a priori (i.e. for cases where there is no ligand for which the binding location relative to the protein is known) are less reliable (Dixon, J. S., "Evaluation of the CASP2 Docking", Proteins: Structure, Function, and Genetics, Supplement-1 (1997), 198–204.). Today, most docking tools model full ligand flexibility, but at least in the faster approaches the binding site is kept rigid. Limited protein side-chain flexibility is exploited by GOLD, which considers rotational flexibility of side chains (Jones et al., J. Mol. Biol., 245, 43–53, 1995), while other approaches use rotomer libraries (Leach, A. R. 1994. Ligand docking to proteins with discrete side-chain flexibility. *Journal of Molecular Biology* 235:345–356); Jackson, R. M., Gabb, H. A. and Sternberg, M. J. E. 1998. Rapid refinement of protein interfaces incorporating solvation: Application to the docking problem. *Journal of Molecular Biology* 276:265–285.) Others still are based on molecular dynamics simulations (Wasserman Z R, Hodge C N. 1996. Fitting an inhibitor into the active site of thermolysin: A molecular dynamics study. *Proteins* 24:227–237.).

Another consideration that influences the accuracy of docking simulations is the solvation of the binding site (Ladbury, J. E. 1996. Just add water! The effect of water on the specificity of protein-ligand binding sites and its potential application to drug design. *Chemistry & Biology* 3:973–980.). Water bound in the ligand site is known to be a critical determinant of ligand specificity for HIV-1 protease (Lam, P. Y. S.; Jadhav, P. K.; Eyermann, C. J.; Hodge, C. N.; Ru, Y.; Bacheler, L. T.; Meek, J. L.; Otto, M. J.; Rayner, M. M.; Wong, Y. N.; Chang, C. H.; Weber, P. C.; Jackson, D. A.; Sharpe, T. R.; and Erickson-Viitanen, S. 1994. Rational design of potent, bioavailable, nonpeptide cyclic ureas as HIV protease inhibitors. Science 263:380–384.) cholera toxin (Merritt, E. A.; Sarfaty, S.; van den Akker, F.; L'Hoir, C.; Martial, J. A.; and Hol, W. G. 1994, Crystal structure of cholera toxin B-pentamer bound to receptor GM1 pentasaccharide. *Protein Science* 3(2): 166–175), and other proteins, and is a ubiquitous component in molecular recognition (Raymer, M. L.; Sanschagrin, P. C.; Punch, W. F.; Venkataraman, S.; Goodman, E. D.; and Kuhn, L. A. 1997. Predicting conserved water-mediated and polar Ligand interactions in proteins using a k-nearest-neighbors genetic algorithm. *Journal of Molecular Biology* 265:445–464). For the docking tool FlexX, a technique called the particle concept has been recently proposed, which adds water molecules at favorable positions during the incremental construction of the ligand in the binding site (Rarey, M.; Kramer, B.; and Lengauer, T. 1999. The particle concept: Placing discrete water molecules during protein-ligand docking predictions. *Proteins: Structure, Function, and Genetics* 34:17–28.). This method was tested for 200 protein-ligand complexes and the accuracy of the predicted binding modes increased for several cases, including HIV protease. A different approach has been introduced for database screening using DOCK: here, the molecules in the database are solvated, which improves the ranking for known ligands and filters out molecules with inappropriate charge states and sizes in comparison to screening without solvation (Shiochet, B. K.; Leach, A. R.; and Kuntz, I. D. 1999. Ligand solvation in molecular docking. *Proteins: Structure, Function, and Genetics* 34:4–16.).

Most docking programs are still too computationally intensive to be used for practical small molecule databases. If a docking program takes approximately one minute per compound, which is about the lower limit used by the fastest docking tools, it would take approximately one week to screen a database of approximately 10,000 compounds. Since it is more efficacious to screen as diverse a set of molecules as possible, computational screening methods preferably should be effective on databases containing millions of compounds. Hence, there is a need for a computational screening method which can effectively screen a database containing a million compounds within a reasonable period of time.

SUMMARY

The inventor has identified new methods for identifying molecules that may bind to a target molecule, and methods described in this patent may be implemented in a computer. In this section we summarize various aspects of these methods and below in the Detailed Description Section we present a more comprehensive description of the methods and their implementation and uses.

One of the methods described in this patent is a method for determining whether a candidate molecule may be docked to a target molecule comprising the steps of: (a) determining a pseudo-energy function, E, between a target molecule and a candidate molecule for one or more of the possible positions $P_i$ of each atom, i, comprising the candidate molecule; (b) determining a function for the partial derivatives of E with respect to $P_i$ for each atom i; (c) determining an initial set of geometric parameters, $Q_j$, describing the conformation of the candidate molecule; (d)

determining partial derivatives of $P_i$ with respect to one or more of the $Q_j$; (e) determining the dot product of $$\frac{\partial E}{\partial P_i} \cdot \frac{\partial P_i}{\partial Q_j}$$

for one or more of the $Q_j$; (f) summing each dot product determined in part e over the i atoms comprising the candidate molecule, thereby determining partial derivatives of E as a function of the geometric parameters comprising the set Q; (g) calculating a new set of geometric parameters based on the set of geometric parameters and the partial derivative of E as a function of the geometric parameters calculated in step f; (h) calculating a pseudo-energy for the candidate molecule with a conformation described by the new set of geometric parameters; (i) identifying the candidate molecule as docked if the pseudo-energy is less than a threshold energy; and (j) if the pseudo-energy is not less than a threshold energy, repeating steps d through j until a criteria is satisfied. In one version of this method, the criteria used in step j include (i) the difference in pseudo-energy in going from one iteration of steps d through j to the next is less than a cutoff energy, or (ii) the number of iterations of steps d through j exceeds a cutoff number.

In this method, in general, successful docking may be determined if the pseudo-energy reaches a threshold energy level. Typical threshold energy levels range from −5.0 kcal/mol to −5.0 kcal/mol. The pseudo-energy and its derivatives may be expressed either as a continuous function or as a finite field. When expressed as a finite field, the pseudo-energy and derivatives can be calculated in advance and used for docking each of the molecules in the set of candidate molecules without recalculation. This allows the computationally intense calculation over of the substituent parts or atoms of the target to be performed only once.

In one version of this method, the conformation space of the candidate molecule is represented in a rotatable bond representation. This representation allows efficient calculation of the derivatives of the positions of the substituent parts of the candidate molecule.

Another of the methods described in this patent is a method for identifying from a set of candidate molecules one or more candidate molecules that may bind to a target molecule, where an individual candidate molecule in the set of candidate molecules comprise one of more substituent parts selected from a set of substituent parts and an individual candidate molecule in the set of candidate molecules is described by one or more geometric parameters, the method comprising the steps of (1) for each substituent part in the set of substituent parts, calculating as a function of possible positions of the substituent part a spatial partial derivative of a pseudo-energy with respect to the position of the substituent part; (2) for each candidate molecule in the set of one or more candidate molecules, identifying an initial set of values for the geometric parameters; (3) for each candidate molecule in the set of one or more candidate molecules, determining if there is a set of values of the geometric parameters for which the candidate molecule and target molecule have a pseudo-energy meeting a pre-selected criteria by varying the values of the geometric parameters, where the values of the geometric parameters are varied depending on the partial derivatives of a pseudo-energy with respect to the values of the geometric parameters, and where the derivatives of the pseudo-energy with respect to the values of the geometric parameters is calculated from the spatial partial derivative of the pseudo-energy with respect to the positions of the substituent parts and derivative of the position of a substituent part relative to the target molecule with respect to the geometric parameters; and (4) for each candidate molecule in the set of one or more candidate molecules, if there exists a set of values of the geometric parameters for which the candidate molecule and target molecule have a pseudo-energy meeting a pre-selected criteria, identifying the candidate molecule as a molecule that may bind to the target molecule.

In one version of this method, representing a geometric parameter by the symbol $Q_j$, representing the positions of the substituent parts in a candidate molecule by $P_i$, and representing the pseudo-energy by E, the derivative of the pseudo-energy with respect to the values of the geometric parameters i.e., $\partial E/\partial Q_j$, is given by $$\frac{\partial E}{\partial Q_j} = \sum_i \frac{\partial E}{\partial P_i} \cdot \frac{\partial P_i}{\partial Q_j}$$

where the sum over i is over all substituent parts in a given candidate molecule.

Generally, the set of candidate molecules may be of any size. In one version of the methods described in this patent, the methods may be used for analyzing sets of candidate molecules, including but not limited to sets including from 2 to 100,000 members, sets including from 2 to 500,000 members, sets including from 2 to 1,000,000 members, sets including from 2 to 2,000,000 members, sets including from 2 to more than 2,000,000 members, sets including more than 50,000 members, sets including more than 100,000 members, sets including more than 500,000 members, sets including more than 1,000,000 members, and sets including more than 2,000,000 members. In one version of the methods described in this patent, the set of one or more candidate molecules includes two or more candidate molecules.

Generally the geometric parameters used for describing the candidate molecules may be any set of parameters capable of describing the geometry of the candidate molecule and the position of the candidate molecule relative to the target molecule. In one version of the methods described in this patent and described in more detail in the Detailed Description section, the geometric parameters include translational parameters, rotational parameters, and rotatable bond parameters.

Generally, the substituent parts of the candidate molecules may be any portion of the molecules, including but not limited to, individual atoms in the molecules, groups of atoms in the molecules, individual portions of high electron density in the molecules (for example, lone pairs). In one version of the methods described in this patent, the substituent parts are individual atoms or groups of atoms. In another version, the substituent parts are individual atoms.

The methods described in this patent may be implemented in a computer system and may be embodied in a computer readable medium.

DETAILED DESCRIPTION OF THE INVENTION

The inventor has discovered new methods for identifying molecules that may bind to target molecules and in this section we describe (1) specific aspects of the methods (2) implementation of the methods, including implementation in a computer system, and (3) general uses of the methods.
Target Molecules and Candidate Molecules The methods described in this patent may be used to identify candidate molecules that may bind to a target molecule. Generally the target molecule may be any molecule or molecular fragment for which it is possible to calculate a pseudo-energy field (from which partial derivatives with respect to substituent positions may be calculated) for the pseudo-energy of a substituent part of a candidate molecule in the presence of the target molecule. The target molecule may include a complex of one or more molecules or molecular fragments. Target molecules include but are not limited to organic molecules, inorganic molecules, organometalic molecules, neutral molecules, radicals, cations, anions, ionic salts, coordination compounds and molecular fragments of any of the foregoing. Specific target molecules that may be used include but are not limited to proteins, enzymes, and nucleic acids.

Examples of target molecules that are a complex of one or more molecules or molecular fragments include but are not limited to a complex of one or more protein molecules, and a solvated protein molecule.

Many of the methods described in the Background Section are specific to calculations of ligand or small-molecule docking to a protein, and the descriptions thus indicate that the target is a protein. This disclosure in the Background Section is in no way intended to limit the definition of target molecule presented in the Summary Section and this Detailed Description Section.

Generally the candidate molecules may be any molecule or molecular fragment.

Candidate molecules include but are not limited to organic molecules, inorganic molecules, organometalic molecules, neutral molecules, radicals, cations, anions, ionic salts, coordination compounds and molecular fragments of any of the foregoing. Specific sets of candidate molecules include but are not limited to libraries of commercially available or synthetically feasible drug-like small molecules, databases of synthetic reactants, building block compounds, databases of peptides or polysaccharides.

Calculation of Pseudo-Energy

In the methods described in this patent, spatial partial derivatives of a pseudo-energy with respect to the positions of substituent parts in a candidate molecule are calculated. Generally, the pseudo-energy may be any function of the position of a candidate molecule substituent part relative to the position of the target molecule. Pseudo-energy functions that may be used include but are not limited to a function calculated as the sum of contributions due to the interaction of the candidate molecule substituent part and one or more substituent parts in the target molecule.

As one non-limiting example, pseudo-energy may include only contributions from those substituent parts in the target molecule that are within some distance of the candidate molecule substituent part. In a preferred but non-limiting example, the pseudo-energy is calculated as the sum of contributions from atoms in the target molecule that are within a preselected distance of the candidate molecule substituent part.

Generally, the substituent parts of the target molecule that may be used in the calculation of the pseudo-energy include any portion of the target molecule, including but not limited to atoms, groups of atoms, bonds, and portions of high electron density such as lone pairs. In one version of the methods described in this patent, the substituent parts in the target molecule are the atoms in the target molecule.

Substituent Parts of the Candidate Molecules

Generally, the substituent parts of the candidate molecules that may be used in the calculation of the pseudo-energy include any portion of the candidate molecules, including but not limited to atoms, groups of atoms, bonds, and portions of high electron density such as lone pairs. In one version of the methods described in this patent, the substituent parts in the candidate molecules are the atoms in the candidate molecules.

One Specific Method that May Be Used for Identifying Candidate Molecules that May Bind to a Target Molecule The following sections include a description of one specific method that may be used for identifying candidate molecules that may bind to a target molecule.

In these examples, the substituent parts of the candidate molecules are the atoms contained in the substituent molecules. As described elsewhere in this patent, the substituent parts of the candidate molecules that may be used are not limited to atoms.

In these examples, the substituent parts of the target molecule used in the calculation of the pseudo-energy are all of the atoms in the target molecule. As described elsewhere in this patent, the substituent parts of the target molecules that may be used are not limited to atoms and generally it is not necessary to include the contribution from all of the substituent parts in the target molecule.

In addition, these examples include some description indicating that the target molecules may preferably be proteins. As described elsewhere in this patent, the target molecules that may be used are not limited to proteins.

In addition, these examples include the steps of determining the 3-D coordinates of each atom in a target molecule and determining the coordinates of each atom in a candidate molecule. As described elsewhere in this patent, the methods described in this patent are not limited to methods that include these steps. These steps may be used in specific non-limiting examples of the methods described in this patent.

Determining the 3-D Coordinates of Each Atom in a Target

A first step in a method according to the invention determines the 3-D, atomic coordinates, of each atom in the target molecule. The atomic coordinates of the target molecule may be obtained by means known in the art, including, X-ray crystallography, nuclear magnetic resonance (NMR) analysis, computational modeling or structure data banks, such as the Protein Data Bank (PDB). The atomic coordinates may be expressed in any 3-D coordinate system. Additionally, the coordinates of the target molecule may include or be modified by the presence of coenzymes, metal ions, glycosyl moieties, solvation shell water molecules, and other small organic or inorganic molecules that are important to determining protein structure and function.

In general, the positions of hydrogen atoms in the target molecule may not be determined by experimental methods such as X-ray crystallography and NMR, nor are hydrogen coordinates generally available from protein structure data banks such as PDB. Accordingly, the atomic coordinates of a hydrogen atom may be estimated based upon the atomic coordinates of the amino acid residues to which a hydrogen atom is associated.

Determining a Pseudo-energy Function Between a Target and any Candidate Molecule A second step determines a pseudo-energy function for the target and a candidate molecule. Alternatively, a pseudo-energy function may be calculated for a sub-part of the target, such as the active site or a binding region of the target, and a candidate molecule. In general, the pseudo-energy function for a target and a candidate molecule may be formed from the sum of different interaction terms, each of which quantifies a distinct interaction between the target and one or more atoms of a candidate molecule. These terms include, but are not limited to, long range electrostatic forces which may be represented by $1/r$ or $1/r^2$ terms, van der Waals ("VDW") interactions which may be represented by a 6–12 Lennard-Jones potential or other model, and hydrophobicity interactions modeled by proximity of like or unlike portions of the molecule to the target molecule. An exemplary pseudo-energy function between a target and a candidate molecule comprised of i atoms may be represented by:

$$E = E_{ELECT} + E_{VDW} + E_{HBOND} + E_{HYDOPHOB} \qquad 1$$

where E is the total pseudo-energy between the target and a candidate molecule. $E_{ELECT}$, $E_{VDW}$, $E_{HBOND}$, $E_{HYDOPHOB}$ are the respective interaction terms characterizing the electrostatic, van der Waals, hydrogen-bonding and hydrophobic contributions to the pseudo-energy E. The pseudo-energy function shown above is said to have no interaction cross terms. An interaction cross term is an interaction term which can be decomposed into a product of two separate interaction terms. When a pseudo-energy function has no interaction cross terms, mathematical operations on the pseudo-energy function, such as taking its derivative, can be performed separately on each term and then added. Depending upon the interaction term, each interaction term, may be formed by summing interaction terms characterizing the interaction between the target and each atom of the candidate molecule over all the atoms of the candidate molecule. For example, for a candidate molecule comprising i atoms, $E_{ELECT}$ may be written as $$E_{ELECT} = \sum_i E_i,$$

where $E_i$ characterizes the interaction between the target and the i'th atom of a candidate molecule. Instead of a continuous pseudo-energy function, a pseudo-energy function may be represented discretely as a field.

A field representation of a pseudo-energy function is a predefined, regular set of points in space at which the pseudo-energy function is sampled. A pseudo-energy field representation is made by generating a 3-D grid over a volume of interest. In general, grids may be expressed in any geometric space, including, but not limited to, Cartesian coordinates, cylindrical coordinates, or spherical coordinates.

Separate fields or grids may be calculated for each interaction term of a pseudo-energy function. For other interaction terms, such as a van der Waals interaction term, a plurality of fields may be calculated. In the case of the van der Waals interaction between a target and a candidate molecule, separate fields may be formed for each type of atom. Grid intervals may range from 0.01 Å to 1.5 Å with 0.1 Å to 0.5 Å being preferred. In general grid intervals should be chosen based upon the characteristics length scales of an interaction term. For example, the Lennard-Jones 6–12 potential represents an attractive force when the two atoms are not close. As the atoms become very close, the potential becomes repulsive, and varies steeply as $R^{-12}$. Correctly modeling the repulsive force at close range requires a fine grid size of 0.2 Å or less. Conversely, the electrostatic potential varies uniformly as $R^{-2}$ or $R^{-1}$, and can be effectively modeled with a grid spacing of 0.5 Å or greater. If the target contains a transition metal, a field could be defined that characterizes the special stabilization in the vicinity of the transition atom for certain atoms or groups of atoms in the target structure. In general, grid intervals are set small enough to afford reasonable estimates of the energy at all points within the field. Decreasing the grid interval beyond a certain point will not increase the accuracy but will increase the computation time involved in setting up the grid, and will increase the memory requirements for storing the grid.

Determining the Partial Derivatives of the Pseudo-energy Function E with Respect to the Position of any Possible Atom Comprising a Candidate Molecule A third step determines the partial derivative of a pseudo-energy function E with respect to the positions $P_i$ of the atoms comprising a candidate molecule. Any of the techniques for calculating derivatives may be used, with analytical methods being preferred over numerical techniques because of their computational efficiency. Typically, the first derivatives are used. Some optimization techniques also utilize second derivatives of the pseudo-energy. When E is represented by a field, $$\frac{\partial E}{\partial P_i}$$

represents a force field (and therefore a vector field) over the range of potential positions which an arbitrary atom comprising a candidate molecule might occupy. Since a database of candidate molecules may comprise j different types of atoms (where type may be denoted by element and charge), j force fields are calculated. In one method according to the invention, $$\frac{\partial E}{\partial P_i}$$

is calculated once, for each possible value j and for each possible position $P_i$, before screening a database of candidate molecules for potential docking. Pre-calculating and saving all potential $$\frac{\partial E}{\partial P_i}$$

yields significant computational efficiencies when screening a large number of candidate molecules.

Determining the 3-D Coordinates of a Candidate Molecule

A fourth step determines the atomic coordinates of each atom comprising the candidate molecule. Such coordinates may be obtained by structural analysis of its unbound, crystallized structure, taken from crystal databases such as the Cambridge Crystallographic database, taken from theoretical structure calculations including semi-empirical techniques, or ab initio techniques, or from template based 3-D structure generation software like CONCORD (licensed by Tripos Inc.—1699 South Hanley Road, St. Louis, Mo. 63144-2913, phone: 314-647-1099) or CORINA (Available from the University of Erlangen, or other techniques. Atomic charges, if present on a constituent atom of a molecule, may be determined by molecular orbital calculation methods such as MNDO, AMI or MOPAC (available from Schrödinger, 1500 S.W. First Avenue, Suite 1180, Portland, Oreg. 97201, Phone: (503) 299-1150), or by less rigorous techniques such as that of Gasteiger et al (J. Gasteiger, M. Marsili, "A New Model for Calculating Atomic Charges in Molecules", Tetrahedron Lett., 3181–3184 (1978)).

Determining the Conformation Space of a Candidate Molecule

A fifth step determines a conformational space of a candidate molecule based upon the original 3-D, spatial coordinates of the lead molecule determined in step four above. One method of determining a conformational space of a candidate molecule, referred to as the rotatable bond representation, represents any candidate molecule as a set of three rotational parameters (R) characterizing rotation of the candidate molecule as a whole about three axes; three translational parameters (T) characterizing translation of the candidate molecule in three directions and rotatable bond parameters (B) characterizing internal rotation of a candidate molecule about its dihedral angles. The coordinate system for determining translation and rotation of the molecule as a whole is usually defined at or near the center-of-mass of the candidate molecule. Although, in principle any set of geometric parameters which characterizes the conformational space of a candidate molecule may be used in the methods according to the invention, the rotatable-bond representation offers a computational advantage. Other representations of a candidate molecule, such as a Cartesian representation, which either explicitly or implicitly reference bond lengths and bond angles, require calculation of bond stretching and bending energies. Since the rotatable-bond representation has fixed bond length and bond angles, no such computationally expensive calculations are required.

Determining the Partial Derivatives of the Pseudo-energy Function with Respect to the Geometric Parameters Defining the Conformational Space A sixth step determines the partial derivatives of the pseudo-energy function with respect to the geometric parameters defining the conformational space. These partial derivatives may then be used in the next step to determine whether a given candidate molecule may be docked to a target and if so, what is docking geometry between the two.

The methods according to the invention are applicable without regard to the coordinate system used to represent the conformational space of a candidate molecule. If the position of the i'th atom, of a candidate molecule is denoted as $P_i$, the partial derivative of a pseudo-energy function E, with respect to an arbitrary geometric parameter defining the conformational space of a candidate molecule, Q, may be generally represented as the dot product:

$$\frac{\partial E}{\partial Q_j} = \frac{\partial E}{\partial P_i} \cdot \frac{\partial P_i}{\partial Q} \qquad 2$$

If the pseudo-energy and derivative functions are represented as grids, the derivative $$\frac{\partial E}{\partial P_i}$$

is taken as that at the nearest grid point. Once the partial derivatives of the pseudo-energy with respect to the geometric parameters are calculated, they may be used to iteratively minimize the relative geometry of a candidate molecule to determine whether a candidate molecule may be docked to a target.

When a candidate molecule is represented in the rotatable bond representation, the set of geometric parameters characterizing the conformational space of the molecule comprises translational parameters (T), rotational parameters (R), and rotatable bond parameters (B). Consider a candidate molecule comprising B rotatable bonds and where the position of each atom $a_i$, is denoted as $P_i(T,R,B)$.

In accordance with Equation 2, the partial derivative of the pseudo-energy between the target and a candidate molecule with respect to translation of the candidate molecule in the direction of the x-axis may be determined by:

$$\frac{\partial E}{\partial T_x} = \sum_i \left( \frac{\partial E}{\partial P_i} \cdot \frac{\partial P_i}{\partial T_x} \right) \qquad 3$$

The latter term $$\frac{\partial P_i}{\partial T_x}$$

is the unit vector (1,0,0). Likewise, $$\frac{\partial P_i}{\partial T_y}$$

is the unit vector (0,1,0) and $$\frac{\partial P_i}{\partial T_z}$$

is the unit vector (0,0,1). Thus the overall derivative with respect to translation is:

$$\frac{\partial E}{\partial T} = \sum_i \frac{\partial E}{\partial P_i} \qquad 4$$

Any manner of calculating $$\frac{\partial E}{\partial P_i}$$

may be employed.

$$\frac{\partial E}{\partial P_i}$$

may be retrieved from a pre-calculated grid as described above based on the position of atom i, or $$\frac{\partial E}{\partial P_i}$$

may be calculated on the fly for the position of each atom using the pseudo-energy function.

Similarly, the partial derivative of the pseudo-energy between the target and a candidate molecule with respect to rotation of the candidate molecule along an axis through the rotational center and parallel to the x-axis may in general be determined by:

$$\frac{\partial E}{\partial R_x} = \sum_i \frac{\partial E}{\partial P_i} \cdot \frac{\partial P_i}{\partial R_x} \qquad 5$$

where $$\frac{\partial P_i}{\partial R_x}$$

represents the partial derivative of the position of the i'th atom with respect to rotation about the axis parallel to the x-axis. The derivative of the position of atom i with respect to the rotation of a candidate molecule about this axis may be determined by the cross product:

$$\frac{\partial P_i}{\partial R_x} = D i \times (1, 0, 0) \qquad 6$$

where $D_i$ represents the vector connecting $P_i$ to the rotational center. Generally, the rotational center may be any point in space. In one preferred version of the methods described in this patent, the rotational center is chosen to be at or near the center of mass of the candidate molecule. The derivatives of the $P_i$ with respect to rotation about the axes through the rotational center and parallel to the y-axis and z-axis can be determined similarly.

Lastly, the partial derivative of the pseudo-energy between a target and a candidate molecule with respect to a rotation $B_b$ about a rotatable bond b, may be expressed as:

$$\frac{\partial E}{\partial \theta_b} = \sum_i \frac{\partial E}{\partial P_i} \cdot \frac{\partial P_i}{\partial B_b} \qquad 7$$

where, $$\frac{\partial P_i}{\partial B_b}$$

is the partial derivative of $P_i$, with respect to the rotation angle $B_b$ of the b'th rotatable bond.

Another aspect of the invention is a method of efficiently calculating the derivative $$\frac{\partial P_i}{\partial B_b},$$

and thus a method of efficiently calculating the derivative of the pseudo-energy between a target and candidate molecule with respect to rotation about a rotatable bond. When a rotatable bond angle is changed, only the atoms connected to one end of the bond will move. The atoms connected to stationary end of the bond do not move, and the derivatives of their positions with respect to this rotation are zero. For the atoms that do move, the derivative $$\frac{\partial P_i}{\partial B_b}$$

may be calculated from the following method. A first step determines a unit vector, $\mu_b$, along the b'th rotatable bond. A second step, determines the vector $D_{b,i}$, connecting the end of the b'th rotable bond to the position of the i'th atom. A third step, determines the cross product $\mu_b \times D_{i,b}$, thereby determining $$\frac{\partial P_i}{\partial B_b}.$$

Alternatively, other mathematical methods that are equivalent to calculating the cross product may be used.

Determining Whether a Candidate Molecule Maybe Docked to a Target

A seventh step iteratively minimizes the pseudo-energy function as function of the geometric parameters defining the conformational space of the candidate molecule using the partial derivatives of the pseudo-energy function with respect to the geometric parameters. In an iterative minimization of the pseudo-energy function, the geometric parameters representing the conformational space of the candidate molecule are iteratively varied until the pseudo-energy reaches a threshold level. At this threshold energy, the candidate molecule and target may be considered docked. The docked conformation of the candidate molecule is characterized by the particular set of geometric parameters of the candidate molecule corresponding to the threshold pseudo-energy. Typically, threshold energy levels for docking are between −5.0 kcal/mol and −15.0 kcal/mol. In general, the methods according to the invention may employ any minimization method to iteratively minimize the pseudo-energy function as a function of the geometric parameters used to represent the conformational space of the candidate molecule. Suitable minimization methods include, but are not limited to, BFGS, Steepest Descent, and conjugate gradient (Shanno, D. F. *Conjugate gradient methods with inexact searches*. Mathematics of Operations Research 3-3, 244–256) methods. The Steepest Descent method uses the first derivative of the pseudo-energy as a function of the geometry of the candidate molecule. In some systems, like the Conjugate Gradient and BFGS methods, which consider both the first and second derivatives of the pseudo-energy as a function of the geometry of the candidate molecule, have been shown in some cases to have better convergence behavior than the methods which only calculate first derivatives of the pseudo-energy. To avoid local minimums of the pseudo-energy function, the docking calculation should be initialized for a number of different initial conformations of the candidate molecule.

The methods according to the invention provide a very efficient scheme for searching a database of candidate molecules because the computationally intensive steps of generating the pseudo-energy function and calculating the derivative of the pseudo-energy function as a function of positional parameters may be performed at the beginning of a database search.

A method for Searching a Database of Candidate Molecules to Determine Whether any Candidate Molecule May Be Docked to a Target In a first step, the 3-D coordinates of each atom in the target are determined. In a second step and third step, the computationally intensive calculations of generating the pseudo-energy function and calculating the derivative of the pseudo-energy function as a function of positional parameters are performed. In a fourth step, each candidate molecule in the database is tested to determine whether it may be docked to target. As detailed above, successful docking may be determined by reference to a threshold energy cut-off. Alternatively, the database search may be started with a target number of hits, and the energy threshold may be automatically adjusted to lower values as the search proceeds and better fitting structures are found. If the outcome of the potential docking test fails, the first candidate molecule may be tested again with a different initial conformation in order to assure that the candidate molecule did not become trapped in a local minimum of the pseudo-energy function. In general, there is no upper limit to how many times a candidate molecule may be test docked with different initial conformations. One skilled in the art would ordinarily select an upper cut-off for the number of potential docking tests of a given candidate molecule based upon the size of the database, the relative acceptability of false-negatives and the topography of the pseudo-energy function.

Implementation of the Methods

The methods described in this patent may be implemented using any device capable of implementing the methods. Examples of devices that may be used include but are not limited to electronic computational devices, including computers of all types. Examples of computer systems that may be used include but are not limited to a Pentium based desktop computer or server, running Microsoft NT, or a Linux based operating platform such as distributed by Red Hat, Inc., or a suitable operating platform, with an enterprise class database. Such computer systems may be readily purchased from Dell, Inc. (Austin, Tex.), Hewlett-Packard, Inc., (Palo Alto, Calif.) or Compaq Computers, Inc., (Houston, Tex.). Generally any enterprise class database software may be used including but not limited to Oracle's 8i (Redwood City, Calif.) or International Business Machine's DB2 (Armonk, N.Y.). When the methods described in this patent are implemented in a computer, the computer program that may be used to configure the computer to carry out the steps of the methods may be contained in any computer readable medium capable of containing the computer program. Examples of computer readable medium that may be used include but are not limited to diskettes, hard drives, CD-ROMs, DVDs, ROM, RAM, punch cards and other memory and computer storage devices. The computer program that may be used to configure the computer to carry out the steps of the methods may also be provided over an electronic network, for example, over the internet, world wide web, an intranet, or other network.

In one example, the methods described in this patent may be implemented in a system comprising a processor and a computer readable medium that includes program code means for causing the system to carry out the steps of the methods described in this patent. The processor may be any processor capable of carrying out the operations needed for implementation of the methods. The program code means may be any code that when implemented in the system can cause the system to carry out the steps of the methods described in this patent. Examples of program code means include but are not limited to instructions to carry out the methods described in this patent written in a high level computer language such as C++, Java, or Fortran; instructions to carry out the methods described in this patent written in a low level computer language such as assembly language; or instructions to carry out the methods described in this patent in a computer executable form such as compiled and linked machine language.

The output from an implementation of the methods described in this patent may be embodied in any article of manufacture capable of containing the output and may also be embodied in computer storage or memory devices capable of containing the output. Examples of articles of manufacture that may be used include but are not limited to diskettes, hard drives, CD ROMs and DVDs. Output from implementation of the methods described in this patent may also be provided over an electronic network, for example, over the internet, world wide web, an intranet, or other network. In such a case, a user of the information may access the information through any device capable of transmitting the information to the user, including but not limited to computer monitors, CRTs, telephones, projection devices, paper images and text. A person becoming aware of the information generated as an output from the methods described in this patent may use the information in a variety of ways including the uses described in the next section. A person may become aware of the information generated as an output from the methods described in this patent in a variety of ways including but not limited to accessing the information via a computer network, accessing the information telephonically, and accessing the information in written form.

Uses of the Methods

The methods described in this patent may be used in a variety of ways including but not limited to identification of molecules that may bind to a target molecule and may therefore be good candidates for further research and development in areas such as, but not limited to, use as pharmaceuticals or for other uses such as herbicides, fungicides, pesticides, chemical weapons; methods for identifying classes of compounds or compounds including particular structural motifs that may preferentially bind to a target molecule such as but not limited to peptides, polysaccharides, sugars, and nucleic acids including but not limited to DNA, and RNA.

The examples described in this patent are for illustrative purposes only and various modifications or changes will be suggested to persons killed in the art and are to be included within the disclosure in this application and scope of the claims. all publications, patents and patent applications cited in this patent are hereby incorporated by reference in their entirety for all purposes to the same extent as if each individual publication, patent or patent application were specifically and individually indicated to be so incorporated by reference.

What is claimed is:

1. A method for determining if a candidate molecule is docked to a target molecule, the method comprising the steps of:
   a. determining a pseudo-energy function, E, between a target molecule and a candidate molecule for one or more of the possible positions $P_i$ of each atom, i, comprising the candidate molecule;
   b. determining a function for the partial derivatives of E with respect to $P_i$ for each atom i;
   c. determining an initial set of geometric parameters, $Q_j$, describing the conformation of the candidate molecule;
   d. determining partial derivatives of $P_i$ with respect to one or more of the $Q_j$;
   e. determining the dot product of $$\frac{\partial E}{\partial P_i} \cdot \frac{\partial P_i}{\partial Q_j}$$

for one or more of the $Q_j$;
   f. summing each dot product determined in part e over the i atoms comprising the candidate molecule, thereby determining partial derivatives of E as a function of the geometric parameters comprising the set Q;
   g. calculating a new set of geometric parameters based on the partial derivatives of E as a function of the geometric parameters calculated in step f;
   h. calculating a pseudo-energy for the candidate molecule with a conformation described by the new set of geometric parameters;
   i. if the pseudo-energy is less than a threshold energy, identifying the candidate molecule as docked;
   j. if the pseudo-energy is not less than a threshold energy, repeating steps d through j until a criteria is satisfied.

2. The method of claim 1, wherein step c comprises the steps of (i) specifying initial positions $P_i$ for each atom i of the candidate molecule; and (ii) determining the initial conformational space of the candidate molecule based upon the initial positions of each atom of the candidate molecule.

3. The method of claim 1, wherein the criteria in step j is (i) the difference in pseudo-energy in going from one iteration of steps d through j to the next is less than a cutoff energy, or (ii) the number of iterations of steps d through j exceeds a cutoff number.

4. The method of claim 1, wherein the derivatives $$\frac{\partial E}{\partial P_i}$$

are precalculated and stored at all points on a grid.

5. A method for determining whether a candidate molecule may be docked to a target, the method comprising the steps of:

a. obtaining the three-dimensional coordinates for one or more atoms of a target molecule;

b. determining a pseudo-energy function, E, between the target molecule and a candidate molecule for one or more of the possible position $P_i$ of each atom, i, comprising the candidate molecule;

c. determining a function for the partial derivative of E with respect to $P_i$ for each atom i;

d. obtaining the three-dimensional coordinates for each atom i of the candidate molecule; thereby determining the initial positions $P_i$ for each atom of the candidate molecule;

e. determining an initial set of geometric parameters, $Q_j$, describing the conformation of the candidate molecule, where the set of geometric parameters comprises translational (T), rotational (R), and rotatable bond (B) parameters;

f. determining partial derivatives of $P_i$ with respect to the rotation and rotatable bond geometric parameters, using the equations:

$$\frac{\partial P_i}{\partial R_x} = Di \times (1, 0, 0)$$

$$\frac{\partial P_i}{\partial R_y} = Di \times (0, 1, 0)$$

$$\frac{\partial P_i}{\partial R_z} = Di \times (0, 0, 1)$$

where $D_i$ represents the vector connecting $P_i$ to the rotational center, and $$\frac{\partial P_i}{\partial B_b} = \mu_b \times D_{b,i}$$

where $D_{b,i}$ represents the vector connecting $P_i$ to the end of the b'th rotatable bond, and
$\mu_b$ is the unit vector along the b'th rotatable bond;

g. determining the dot product of $$\frac{\partial E}{\partial P_i} \cdot \frac{\partial P_i}{\partial Q_j}$$

for one or more of the $Q_j$;

h. summing each dot product determined in step g over the i atoms comprising the candidate molecule, thereby determining partial derivatives of E as a function of the geometric parameters comprising the set Q;

i. calculating a new set of geometric parameters based on the set of geometric parameters and the partial derivative of E as a function of the geometric parameters calculated in step h;

j. calculating a pseudo-energy for the candidate molecule with a conformation described by the new set of geometric parameters;

k. if the pseudo-energy is less than a threshold energy, identifying the candidate molecule as docked;

l. if the pseudo-energy is not less than a threshold energy, repeating steps f through l until a criteria is satisfied.

6. The method of claim 5 wherein the derivatives $$\frac{\partial E}{\partial P_i}$$

are precalculated and stored at all points on a grid.

7. A method for screening a database of candidate molecules for docking with a target molecule comprising the steps of:

a. obtaining the three-dimensional coordinates for one or more atoms of the target molecule;

b. determining a pseudo-energy function, E, between the target molecule and one or more possible position $P_k$ of each atom, k, contained in a set of atoms comprising all atoms contained in candidate molecules in a database of candidate molecules;

c. determining a function of the partial derivative of E with respect to $P_k$ for each atom k in the set of atoms;

d. obtaining the three-dimensional coordinates for each atom i of a candidate molecule in the database of candidate molecules; thereby determining the initial positions $P_i$ for each atom of the candidate molecule;

e. determining an initial set of geometric parameters, $Q_j$, describing the conformation of the candidate molecule, where the set of geometric parameters comprises translational (T), rotational (R), and rotatable bond (B) parameters;

f. determining partial derivatives of $P_i$ with respect to the rotational and rotatable geometric parameter using the equations:

$$\frac{\partial P_i}{\partial R_x} = Di \times (1, 0, 0)$$

$$\frac{\partial P_i}{\partial R_y} = Di \times (0, 1, 0)$$

$$\frac{\partial P_i}{\partial R_z} = Di \times (0, 0, 1)$$

where $D_i$ represents the vector connecting $P_i$ to the rotational center, and $$\frac{\partial P_i}{\partial B_b} = \mu_b \times D_{b,i}$$

where $D_{b,i}$ represents the vector connecting $P_i$ to the end of the b'th rotatable bond, and
$\mu_b$ is the unit vector along the b'th rotatable bond;

g. determining the dot product of $$\frac{\partial E}{\partial P_i} \cdot \frac{\partial P_i}{\partial Q_j}$$

for one or more of the $Q_j$;

h. summing each dot product determined in step g over the i atoms comprising the candidate molecule, thereby determining partial derivatives of E as a function of the geometric parameters comprising the set Q;

i. calculating a new set of geometric parameters based on the partial derivatives of E as a function of the geometric parameters calculated in step h;

j. calculating a pseudo-energy for the candidate molecule with a conformation described by the new set of geometric parameters;

k. if the pseudo-energy is less than a threshold energy, identifying the candidate molecule as docked;

l. if the pseudo-energy is not less than a threshold energy, repeating steps f through l until a criteria is satisfied.

m. repeating steps e through l for each candidate molecule in the database of candidate molecules.

8. The method of claim 7 wherein the derivatives $$\frac{\partial E}{\partial P_i}$$

are precalculated and stored at all points on a grid.

9. A system for determining if a candidate molecule is docked to a target, the system comprising:

a processor; and a computer readable medium having computer readable program code means embodied therein for causing the system to identifying from a set of one or more candidate molecules one or more candidate molecules that may bind to a target molecule, the computer readable program code means comprising: (a) a computer readable program code means for causing a computer to carry out the step of determining a pseudo-energy function, E, between a target molecule and a candidate molecule for one or more of the possible positions $P_i$ of each atom, i, comprising the candidate molecule; (b) a computer readable program code means for causing a computer to carry out the step of determining a function for the partial derivatives of E with respect to $P_i$ for each atom i; (c) a computer readable program code means for causing a computer to carry out the step of determining an initial set of geometric parameters, $Q_j$, describing the conformation of the candidate molecule; (d) a computer readable program code means for causing a computer to carry out the step of determining partial derivatives of $P_i$ with respect to one or more of the $Q_j$; (e) a computer readable program code means for causing a computer to carry out the step of determining the dot product of $$\frac{\partial E}{\partial P_i} \cdot \frac{\partial P_i}{\partial Q_j}$$

for one or more of the $Q_j$; (f) a computer readable program code means for causing a computer to carry out the step of summing each dot product determined in part e over the i atoms comprising the candidate molecule, thereby determining partial derivatives of E as a function of the geometric parameters comprising the set Q; (g) a computer readable program code means for causing a computer to carry out the step of calculating a new set of geometric parameters based on the partial derivatives of E as a function of the geometric parameters calculated in step f; (h) a computer readable program code means for causing a computer to carry out the step of calculating a pseudo-energy for the candidate molecule with a conformation described by the new set of geometric parameters; (i) a computer readable program code means for causing a computer to carry out the step of identifying the candidate molecule as docked if the pseudo-energy is less than a threshold energy; and (j) a computer readable program code means for causing a computer to carry out the step of repeating steps d through j until a criteria is satisfied if the pseudo-energy is not less than a threshold energy.

10. An article of manufacture comprising a computer useable medium having computer readable program code means embodied therein for determining if a candidate molecule is docked to a target, the computer readable program code means comprising: (a) a computer readable program code means for causing a computer to carry out the step of determining a pseudo-energy function, E, between a target molecule and a candidate molecule for one or more of the possible positions $P_i$ of each atom, i, comprising the candidate molecule; (b) a computer readable program code means for causing a computer to carry out the step of determining a function for the partial derivatives of E with respect to $P_i$ for each atom i; (c) a computer readable program code means for causing a computer to carry out the step of determining an initial set of geometric parameters, $Q_j$, describing the conformation of the candidate molecule; (d) a computer readable program code means for causing a computer to carry out the step of determining partial derivatives of $P_i$ with respect to one or more of the $Q_j$; (e) a computer readable program code means for causing a computer to carry out the step of determining the dot product of $$\frac{\partial E}{\partial P_i} \cdot \frac{\partial P_i}{\partial Q_j}$$

for one or more of the $Q_j$; (f) a computer readable program code means for causing a computer to carry out the step of summing each dot product determined in part e over the i atoms comprising the candidate molecule, thereby determining partial derivatives of E as a function of the geometric parameters comprising the set Q; (g) a computer readable program code means for causing a computer to carry out the step of calculating a new set of geometric parameters based on the set of geometric parameters and the partial derivative of E as a function of the geometric parameters calculated in step f; (h) a computer readable program code means for causing a computer to carry out the step of calculating a pseudo-energy for the candidate molecule with a conformation described by the new set of geometric parameters; (i) a computer readable program code means for causing a computer to carry out the step of identifying the candidate molecule as docked if the pseudo-energy is less than a threshold energy; and (j) a computer readable program code means for causing a computer to carry out the step of repeating steps d through j until a criteria is satisfied if the pseudo-energy is not less than a threshold energy.

* * * * *